(12) United States Patent
Schroering, Jr.

(10) Patent No.: US 7,097,453 B1
(45) Date of Patent: Aug. 29, 2006

(54) DENTAL IMPLANT

(76) Inventor: Robert Lewis Schroering, Jr., Advanced Implant Center, 901 DuPont Rd., Louisville, KY (US) 40207

( * ) Notice: Subject to any disclaimer, the term of this patent is extended or adjusted under 35 U.S.C. 154(b) by 209 days.

(21) Appl. No.: 10/404,700

(22) Filed: Apr. 1, 2003

(51) Int. Cl.
*A61C 8/00* (2006.01)

(52) U.S. Cl. .................................... 433/173

(58) Field of Classification Search ............... 433/173, 433/174, 175, 176, 201.1
See application file for complete search history.

(56) References Cited

U.S. PATENT DOCUMENTS

| | | | | |
|---|---|---|---|---|
| 4,723,913 A | * | 2/1988 | Bergman | 433/173 |
| 5,588,838 A | * | 12/1996 | Hansson et al. | 433/173 |
| 6,419,491 B1 | * | 7/2002 | Ricci et al. | 433/173 |
| 6,454,569 B1 | * | 9/2002 | Hollander et al. | 433/173 |

\* cited by examiner

*Primary Examiner*—Melba N. Bumgarner

(57) ABSTRACT

A dental implant having bands on the exterior surface that define grooves of a defined depth and width is described. Near a distal end of the implant, the grooves have a relatively shallow depth. Near a proximal end, the grooves may or may not have a depth about twice as deep as near the distal end.

8 Claims, 1 Drawing Sheet

DENTAL IMPLANT

BACKGROUND

The present invention is a dental implant device designed to minimize tissue loss. The device has a plurality of connective tissue grooves on a stem portion of an abutment section and a plurality of bone locking grooves on a neck section of an implant section, wherein the implant section is proximal to the abutment section.

Dental implants are embedded in the jaw bone and serve to anchor one or more artificial teeth or dentures. Typically, the implant is set in the bone and an abutment is mounted on the implant. As is known in the art, the abutment generally has a first segment that abuts the implant and that is preferably positioned so as to lie within the connective tissue layer, a second segment that abuts the first segment and is preferably positioned so as to lie within the attached epithelial layer, and a third segment that abuts the second segment and is preferably positioned so as to lie within the sulcular epithelial layer. Each of the tissues layers are generally believed to be about 1 mm in depth.

Important to the success of such devices is the rigid anchoring of the implant in the bone, and several journal articles and patents have proposed various methods for achieving rigid anchoring (see U.S. Pat. No. 5,344,457 and incorporated herein by reference). For example, U.S. Pat. No. 4,713,003, issued to Symington et al. describes an implant that has a tapered external body, resulting in a better distribution of the stresses acting on the device in situ than is achieved with cylindrical body implants. U.S. Pat. No. 5,344,457, issued to Pilliar et al, describes an implant that has a body with a non-porous surface on the upper portion of the implant and a porous surface on the lower portion of the implant. The porous surface provides interstices into which bone is permitted to grow once the implant is accommodated within the bone.

As reported in U.S. Pat. No. 6,454,469, issued to Hollander et al, and incorporated herein by reference, it is known to provide a variety of surface effects to enhance osseo-stability of the implant within bone. In the '469 patent a device is taught that has a collar portion consisting of proximal and distal cylindrical sub-segments, one having a surface effect adapted for the promotion of growth of soft tissue and the other adapted for the promotion of bone or hard tissue growth. Specifically, the '469 patent teaches a dental implant having a distal segment with a surface that defines an ordered microgeometric repetitive surface pattern in the form of a multiplicity of alternating ridges and grooves, each having a fixed or established width in a range of about 2.0 to about 25 microns and a fixed or established depth in the range of about 2.0 to about 25 microns.

While the device of the '469 patent recognizes that bone and soft tissue react differently with implant surfaces, it fails to recognize that academic studies have demonstrated that pore sizes of 10 microns or less lead to little or no fibrous ingrowth, and that a pore size of greater than about 30 microns is needed to give right to good blood supply and blood vessel ingrowth. This ingrowth is believed to be a factor in impeding epithelial migration toward the boney region of the implant site, and the less epithelial migration into the site, the lower the probability of infection development.

SUMMARY OF THE PREFERRED EMBODIMENT

The present invention is a dental implant device having a plurality of connective tissue grooves on a stem portion of an abutment section and a plurality of bone locking grooves on a neck section of an implant section, wherein the implant section is proximal to the abutment section. The bone locking grooves may have a depth approximately twice the depth of the connective tissue grooves thereby allowing the implant to be "locked" into the bone with resultant stabilization of the implant. To minimize the risk that contamination can transverse into the implant site, each groove is preferably isolated from its neighboring grooves.

In one embodiment, the stem section is included as part of a one-piece unit combining an abutment with the implant. In an alternative embodiment, the stem section and its related abutment are separate from the implant. For each embodiment, the stem section includes the connective tissue grooves.

The bone locking grooves are positioned on a distal end of the implant. In one embodiment, the bone locking grooves have a depth of about 100 microns and the connective tissue grooves have a depth of about 50 microns.

DETAILED DESCRIPTION OF THE PREFERRED EMBODIMENT

The dental devices depicted in the various Figures are selected solely for the purposes of illustrating the invention. Other and different dental devices may utilize the inventive features described herein as well. The illustrations are not intended to be representative with respect to dimensions.

Figure 1:
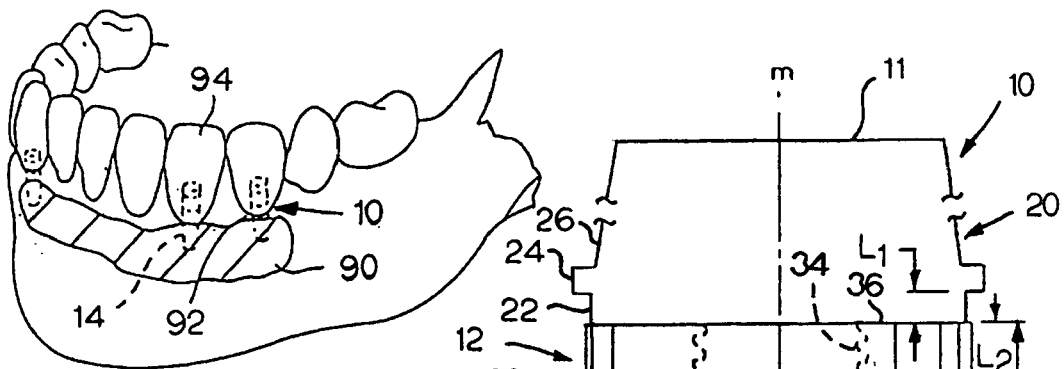
FIG. 1 is a perspective view of a dental device made in accordance with the present invention anchored in a lower jaw bone.
Figure 3:
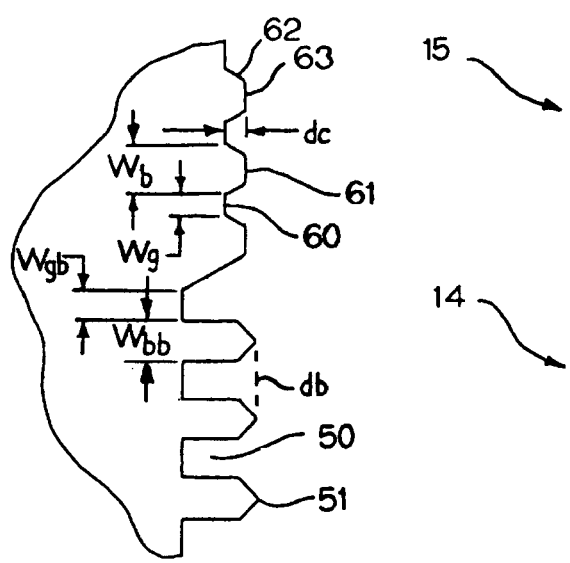
FIG. 3 is a detailed view of the connective tissue rings and grooves of the abutment section and of the bone locking rings and grooves of the implant section of the dental device of FIG. 2.
Figure 2:
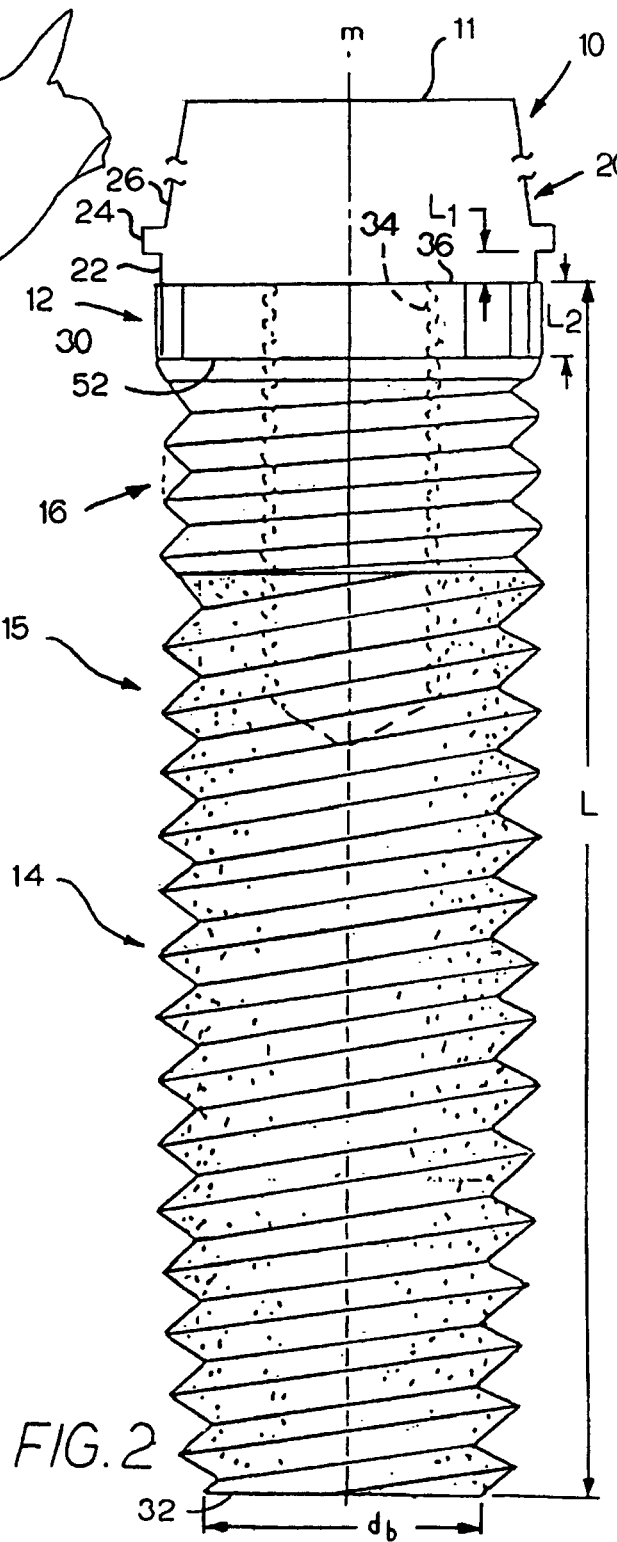
FIG. 2 is a side view of the dental device of FIG. 1.

Reference is first made to FIGS. 1 through 3 in which the dental device constructed in accordance with the present invention is generally noted by the character numeral 10. The dental device 10, which defines a distal abutment end 11 and a proximal end 32, has as major components an abutment section 20 and an implant section 30. The abutment section 20 comprises a first segment or stem 22, a second segment or collar 24, and a third segment or head 26. The stem 22 is adjacent to the implant section 30. The implant section 30 comprises a neck 12 and a body 15. In the embodiment of FIG. 2, the body 15 includes two different types of surface textures for inserting the implant 30 into the bone 90, however, the implant 30 may have any type of surface texture or configuration that is known in the art of dental implants to function as intended. As is known in the art, the implant section 30 includes a bore 34. The implant section 30 has an axial length, L, defined as the distance between an abutment end 36 and the proximal end 32. A midline, m, is defined through the axial center of dental device 10.

As shown in FIG. 1, the dental device 10 is mounted in a cavity 92 bored into the jaw bone 90 of the patient such that the proximal end threaded region 14 extends into the jaw bone 90. After the dental device 10 is anchored in the jaw bone 90, a bridge or artificial tooth 94 can be secured to the device 10, as is known in the art. The device 10 can be formed from any smooth hard material commonly known in the art as being suitable for dental implants. In one embodiment, the device 10 is machined from a titanium alloy. The device 10 can be inserted into the cavity 92 by being screwed in or hammered in, techniques which are known in the art.

As shown in FIGS. 2 and 3, the abutment section 20 is adjacent to the implant section 30 such that the stem 22 abuts the neck 12. When the dental device 10 is properly inserted into the jaw bone 90, the stem 22 will lie essentially at the upper edge of the bone and within a connective tissue layer. The stem 22 comprises a plurality of rings 61 that form a plurality of grooves 60 that circumscribe the stem 22. The stem 22 has length $L_1$ of about 0.2 mm to about 2 mm. Each ring 61 of the band defines an outer diameter and each groove 60 defines an inner diameter. The difference between the outer diameter and the inner diameter defines a connective tissue groove depth, $d_c$. In an embodiment, the groove depth $d_c$ is from about 10 microns to about 250 microns, and in one preferred embodiment, the groove depth is about 50 microns.

The rings 61 circumscribe the stem 22 so as to lie essentially parallel, and preferably equispaced, relative to each other. The rings 61 may lie essentially perpendicular to the midline m, i.e. they can form a series of neighboring rings encircling the stem 22, or they may lay at a slight angle relative to the midline m, thereby giving the stem 22 a "spiraled" appearance. Optionally, the rings 61 may be essentially planar or may have a slight "wave" so as to more closely match the bone contour. The rings 61 serve to isolate the grooves 60 so that bacteria and/or other contaminants cannot transverse the axial length of the dental device 10.

As shown in FIG. 3, each ring 61 has an edge 62 and a face 63, and defines a band width, $w_b$. The angle of the edge 62 relative to the face 63 may vary from a slight angle to essentially a right angle. The edge may be "beveled" or rounded slightly to eliminate sharp edges. Each groove 60 defines a groove width, $w_g$, that can range from about 30 microns to about 150 microns, preferably from about 30 microns to about 145 microns, and more preferably from about 30 microns to about 135 microns. In one embodiment, the band width $w_b$ and groove width $w_g$ and distal end groove depth $d_c$ are essentially identical. In a second embodiment, the band edge 62 is approximately at a right angle to the face 63. In a preferred embodiment, the stem 22 has about 14 grooves 60 covering a length of about 0.7 mm along the stem 22, and the band width $w_b$ and groove width $w_g$ and distal end groove depth dd are each approximately 50 microns. The connective tissue rings 61 and grooves 62 serve to help form a tight band of connective tissue around the stein 22. This can minimize the risk of bacterial invasion and can potentially limit bone loss. This may further mimic the Sharpey fiber attachment that is present on a natural tooth.

Referring again to FIG. 2, the stem 22 lies adjacent to the neck 12 of the implant section 30. The neck 12 comprises a plurality of bone locking grooves 50. The neck 12 and bone locking grooves 50 may form only a relatively short portion along the implant section 30, as shown in FIG. 2, with macro grooves 14 or other surface textures as are known in the art covering the body 15. Alternatively, the neck 12 and bone locking grooves 50 may extend from the stem 22 to the proximal end 32 of implant section 30. In a preferred embodiment, the neck 12 has an axial length, $L_2$, of from about 0.1 mm to about 16 mm.

The bone locking grooves 50 are formed by a plurality of rings 51 similar to the connective tissue band rings 61 and grooves 60. Each bone locking ring 51 defines an outer diameter and each bone locking groove 50 defines an inner diameter. The difference between the outer diameter and the inner diameter defines a bone locking groove depth, $d_b$. The bone locking groove depth $d_b$ may be equal to or less than or, preferably, greater than the connective tissue groove depth $d_c$, and is preferably from about 30 microns to about 150 microns. In one embodiment, the bone locking groove depth $d_b$ is about two times the connective tissue groove depth dc, and in a preferred embodiment the bone locking groove depth is about 100 microns.

Similar to the connective tissue rings 61, the bone locking rings 51 circumscribe the neck 12 so as to lie essentially parallel, and preferably equispaced, relative to each other. The rings 51 may lie essentially perpendicular to the midline m, i.e. they can form a series of neighboring rings encircling the neck 12, or they may lay at a slight angle relative to the midline m, thereby giving the neck 12 a "spiraled" appearance. Optionally, the rings 51 may be essentially planar or may have a slight "wave" so as to more closely match the bone contour. The rings 51 serve to isolate the grooves 50 so that bacteria and/or other contaminants cannot transverse the axial length of the dental device 10. It is anticipated that an embodiment wherein the diameter of the connective tissue rings is less than the diameter of the bone locking rings would demonstrate greater resistance to bacterial infection because the connective tissue could be locked more tightly around the neck 22 of the dental device 10. However, it is not a requirement that the diameter of the connective tissue rings be less than the diameter of the bone locking rings.

The number of bone locking bands 51 and grooves 50 may vary. As shown in FIG. 3, the bands 51 and grooves 50 define a specific band width, $w_{bb}$, and groove width, $w_{gb}$. In one embodiment, the band width $w_{bb}$ is approximately one-half the groove width $w_{gb}$ and approximately one-half the connective tissue groove depth $w_g$. In a preferred embodiment, the bone locking band width $w_{bb}$ is about 50 microns and the groove width $w_{gb}$ and connective tissue groove depth $w_g$ are each approximately 100 microns. The depth of the bone locking grooves is selected to encourage the implant 10 to lock into the cortical layer of bone thereby providing stability to the implant 10 and an increased area for bone ingrowth. These features reduce the risk of bone loss that is demonstrated with prior art implants. As with the connective tissue grooves, the edges of the bone locking grooves may be "beveled" or rounded slightly to eliminate sharp edges.

In the embodiment shown in FIG. 2, the dental device 10 has an essentially cylindrical shape. However, other configurations known in the art, such as implants with a frusto-conical shape, can apply the band and groove technology described herein. As shown in FIG. 2, the dental device 10 is a one-piece unit comprising an abutment section 20 and an implant section 30. Optionally, the dental device 10 may be divided into separate pieces that can be reassembled to create the device 10. For example, it is anticipated that the device 10 could be divided into the abutment section 20 with a separate implant section 30, the division being made along the abutment end 36. The stem 22, neck 12 and other exterior faces of the dental device 10 may have a smooth, porous, coated, treated, textured, roughened, machined or beaded surface comprised of a network of discrete particles which provides interstices into which bone is permitted to grow once implant 10 is accommodated within the bone 90 (such as described in U.S. Pat. No. 6,379,153, issued to Schroering, and incorporated herein in its entirety by reference, or roughened by other techniques known in the art).

Several optional features, known in the art and not shown herein, may be included in the implant 10. For example, the implant 10 may be self-tapping to allow the implant 10 to enter the jaw bone more easily. Further, the implant 10 may include a cutting thread at the interface between the proximal end grooved region 14 and the distal end grooved region 16. Cutting threads are commonly used to help seat the dental implants.

The band and groove design disclosed herein is anticipated to be applicable to implant designs other than the implant depicted in FIG. 2. For example, in the implant described in U.S. Pat. No. 6,379,153 issued to the applicant, the smooth-surfaced neck (44) can be replaced by the bone locking grooved neck 12 taught herein and the abutment section 20, comprising the stem 22 with the connective tissue rings and grooves 50, 51, can be adjoined to the implant (10). The resulting dental device would provide for a tapered body with a beaded finish between the bone locking grooves 16 and the proximal end 32.

It is understood that, in light of a reading of the foregoing description and drawings, those with ordinary skill in the art will be able to make changes and modifications to the present invention without departing from the spirit or scope of the invention, as defined herein. For example, those skilled in the art may accomplish the band and groove patterns by using bands with tips of a different design or configuration.

What is claimed is:

1. A dental device for anchoring in bone said device comprising:
   a. a connective tissue band having an axial length of from about 0.1 mm to about 2.0 mm and comprising a plurality of connective tissue rings circumscribing said connective tissue band thereby forming a plurality of connective tissue grooves, wherein said connective tissue grooves define a groove width of from about 30 microns to about 150 microns, and wherein said connective tissue rings define a first outer diameter and the connective tissue grooves define a first inner diameter, and the difference between said first outer diameter and said first inner diameter defines a connective tissue groove depth, and said connective tissue groove depth is from about 10 microns to about 72.5 microns; and
   b. a bone locking region having a length of from about 0.1 mm to about 16 mm and comprising a plurality of bone locking rings circumscribing said bone locking region thereby forming a plurality of bone locking grooves, wherein the bone locking rings define a second outer diameter and the bone locking grooves define a second inner diameter, and the difference between said second outer diameter and said second inner diameter defines a bone locking groove depth, and said bone locking groove depth is from about 30 microns to about 145 microns; and
   wherein said connective tissue band and said bone locking region are adjacent, and wherein said bone locking groove depth is equal to or greater than about two times said connective tissue groove depth.

2. The dental device of claim 1 wherein said connective tissue rings define a width and said connective tissue grooves define a width, and said connective tissue ring width is essentially equal to said connective tissue groove width.

3. The dental device of claim 2 wherein said connective tissue groove depth is essentially equal to said connective tissue groove width.

4. The dental device of claim 1 wherein said connective tissue grooves are essentially parallel relative to each other.

5. The dental device of claim 1 wherein said bone locking rings are essentially parallel relative to each other.

6. The dental device of claim 1 wherein said connective tissue grooves have a depth of about 50 microns.

7. The dental device of claim 1 wherein said connective tissue grooves cover a length of 0.7 mm.

8. A dental device for anchoring in bone, said device comprising:
   a. a connective tissue band having an axial length of from about 0.1 mm to about 2.0 mm and comprising a plurality of connective tissue rings circumscribing said connective tissue band thereby forming a plurality of connective tissue grooves, wherein said connective tissue grooves define a groove width from about 30 microns to about 150 microns, and wherein said connective tissue rings define a first outer diameter and said connective tissue grooves define a first inner diameter, and wherein a connective tissue groove depth is defined as the difference between said first outer diameter and said first inner diameter and said connective tissue groove depth is about 100 microns; and
   b. a bone locking region having a length of from about 0.1 mm to about 16 mm and comprising a plurality of bone locking rings circumscribing said bone locking region thereby forming a plurality of bone locking grooves, wherein said bone locking rings define a ring width of about 50 microns and said bone locking grooves define a groove width of about 100 microns, and wherein said bone locking rings define a second outer diameter and said bone locking grooves define a second inner diameter, and wherein a bone locking groove depth is defined as the difference between said second outer diameter and said second inner diameter and said bone locking groove depth of up to about 145 microns; and
   wherein said connective tissue band and said bone locking region are adjacent, and wherein said bone locking groove depth is not less than said connective tissue groove depth.

* * * * *